(12) United States Patent
Gale et al.

(45) Date of Patent: Sep. 17, 2013

(10) Patent No.: US 8,535,536 B1

(54) CROSS-FLOW SPLIT-THIN-FLOW CELL

(75) Inventors: Bruce K. Gale, Taylorsville, UT (US); Himanshu Sant, Salt Lake City, UT (US); Venu Madhav, Salt Lake City, UT (US); Srinivas Merugu, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 455 days.

(21) Appl. No.: 12/830,104

(22) Filed: Jul. 2, 2010

Related U.S. Application Data

(60) Provisional application No. 61/223,031, filed on Jul. 4, 2009.

(51) Int. Cl.
*B01D 61/28* (2006.01)

(52) U.S. Cl.
USPC ........ 210/634; 210/198.1; 210/252; 210/258; 210/321.6; 210/321.72; 210/321.75; 210/433.1; 210/643; 210/644; 210/645; 210/646; 210/748.01; 422/500; 422/502; 422/503

(58) Field of Classification Search
USPC .............. 210/198.1, 252, 258, 321.6, 321.72, 210/321.75, 433.1, 634, 643–646, 748.01; 422/500, 502, 503, 504, 505, 507
See application file for complete search history.

(56) References Cited

U.S. PATENT DOCUMENTS

| | | | |
|---|---|---|---|
| 4,737,268 A | 4/1988 | Giddings | |
| 4,894,146 A | 1/1990 | Giddings | |
| 4,894,172 A | 1/1990 | Williams | |
| 5,039,426 A | 8/1991 | Giddings | |
| 5,971,158 A | * 10/1999 | Yager et al. | 209/155 |
| 6,136,171 A | 10/2000 | Frazier et al. | |
| 6,139,746 A | 10/2000 | Kopf | |

(Continued)

FOREIGN PATENT DOCUMENTS

| | | |
|---|---|---|
| EP | 0230899 | 1/1987 |
| WO | WO 2006/138314 | 12/2006 |

OTHER PUBLICATIONS

Contado et al.; Continuous Split-Flow Thin Cell and Gravitational Field-Flow Fractionation of Wheat Starch Particles; Journal of Chromatography A; 2000; pp. 449-460; vol. 871.

(Continued)

*Primary Examiner* — John Kim
(74) *Attorney, Agent, or Firm* — Thorpe North & Western LLP

(57) ABSTRACT

A split thin-flow separations device can include a fluid channel having an inlet zone, an outlet zone, and a transport region between the inlet zone and outlet zone. The inlet zone includes a sample inlet and a carrier fluid inlet which are fluidly separated by an inlet splitter to minimize mixing of fluids from respective inlets in the inlet zone. The transport region can be a substantially open channel. Similar to the inlet zone, the outlet zone can include a sample outlet and a carrier outlet which are fluidly separated by an outlet splitter to segregate portions of a fluid into each of the two outlets as the fluid enters the outlet zone. A plurality of cross-flow inducers can also be oriented along a wall of the fluid channel in the transport region. The cross-flow inducers are oriented to form a cross-flow field across the transport region.

23 Claims, 7 Drawing Sheets

(56) References Cited

U.S. PATENT DOCUMENTS

| | | | |
|---|---|---|---|
| 6,214,221 B1 | 4/2001 | Kopf | |
| 6,315,895 B1 | 11/2001 | Summerton et al. | |
| 6,416,642 B1* | 7/2002 | Alajoki et al. | 204/451 |
| 6,592,821 B1* | 7/2003 | Wada et al. | 422/68.1 |
| 6,596,172 B1 | 7/2003 | Kopf | |
| 6,663,757 B1 | 12/2003 | Fuhr et al. | |
| 6,695,147 B1 | 2/2004 | Yager et al. | |
| 6,803,019 B1* | 10/2004 | Bjornson et al. | 422/66 |
| 6,936,699 B2 | 8/2005 | Peters | |
| 6,946,075 B2 | 9/2005 | Kopf | |
| 7,276,170 B2 | 10/2007 | Oakey et al. | |
| 7,404,490 B2 | 7/2008 | Kennedy et al. | |
| 7,641,865 B2* | 1/2010 | Tonkovich et al. | 422/129 |
| 7,745,221 B2* | 6/2010 | Butler et al. | 436/63 |

OTHER PUBLICATIONS

Springston et al.; Continuous Particle Fractionation Based on Gravitational Sedimentation in Split-Flow Thin Cells; Anal. Chem.; 1987; pp. 344-350; vol. 59.

Giddings; Continuous Separation in Split-Flow Thin (SPLITT) Cells: Potential Applications to Biological Materials; Separation Science and Technology Jul. 1988; pp. 931-943; Issue 8 and 9.

Momi et al.; Behaviour of Environmental Aquatic Nonocolloids when Separated by Split-Flow Thin-Cell Fractionation (SPLITT); Science of the Total Environment; 2008; pp. 317-323; vol. 405.

Williams et al.; Splitter Imperfections in Annular Split-Flow Thin Separation Channels: Effect on Nonspecific Crossover; Anal. Chem.; Mar. 15, 2003; pp. 1365-1373; vol. 75 No. 6.

Williams et al.; Characterization of Nonspecific Crossover in Split-Flow Thin Channel Fractionation; Anal. Chem.; Sep. 15, 2008; pp. 7105-7115; vol. 80 No. 18.

Narayanan et al.; Characterization of a Microfabricated Electrical SPLITT System; Dec. 2004; 109 pages.

Narayanan et al.; A Microfabricated Electrical SPLITT System; Lab Chip; 2006; pp. 105-114; vol. 6.

Performance Characteristics Including Limitations Due to Flow Instabilities in Continuous SPLITT Fractionation; 23 pages.

Sant et al.; Microscale Diffusional Split-Thin-Cell: Protein Separation System; Power Point.

* cited by examiner buffer side outlet carrier side outlet

CROSS-FLOW SPLIT-THIN-FLOW CELL

RELATED APPLICATION

This application claims the benefit of U.S. Provisional Patent Application No. 61/223,031, filed Jul. 4, 2009 and which is incorporated herein by reference.

BACKGROUND

In recent years a number of studies have suggested that the retention of numerous compounds is responsible for enhancing uremic conditions, not just the low molecular weight nitrogenous toxin. According to the European Uremic Toxin (EUTox) workgroup, these compounds, with a relatively diverse nature in terms of molecular weight and properties, are divided into two major groups: protein-bound solutes and middle molecules.

The molecular weight of middle molecules range from 500 to 60000 Da and consist mainly of low molecular weight proteins and peptides (LMWPs). Toxins covered in this class are $\beta$2-microglobulin ($\beta$2M), complement proteins (C3a and Factor D), leptins and pro-inflammatory cytokines. The effect of these toxins can complicate the patient's condition with end stage renal disease. For example, high plasma levels of $\beta$2M (50 fold or more than normal level) have been related to the formation of severely destructive and potentially fatal amyloid deposits, characteristic of dialysis-related-amyloidosis. Similarly, parathyroid hormone (PTH) accumulation in dialysis patients has been related to carpal tunnel syndrome, high blood pressure and secondary hyperparathyroidism.

The effectiveness of the current membrane-based dialysis process is very low in removing $\beta$2M (11.8 KDa) from the blood stream as it requires an increase in pore size of the membrane. The increase in pore size also results in an increase in undesirable loss of useful proteins such as albumin in addition to possible retake of harmful endotoxins from dialysate. For this reason, methods based on hydrophobicity and immunospecificity have been developed, but each of these methods has its own shortcomings. The method based on hydrophobic interaction is not specific. The size of the adsorbent has to be adjusted to prevent removal of albumin or similar proteins. A careful design of the adsorbent bed is required to prevent clogging because of granulocyte and platelet adhesion or damage to the blood cells, due to high shear forces if an adsorbent with very small pores (for high surface area and size exclusion) is used. Methods based on immunospecific antibodies also suffer from similar problems. Furthermore, there are high costs involved in the development and purification of the antibodies. In addition, methods based on absorbent beds or affinity columns may result in small particulate material contamination of the blood stream, which may lead to thrombi and pulmonary emboli formation. Both approaches lack the ability to meet the high throughput requirements associated with hemodialysis.

Thus, current options are deficient such that a better toxin (such as $\beta$2M) removal system for hemodialysis applications is desirable. In one study, a 5% improvement in mortality was achieved with only a 10% increase in $\beta_2$-microglobulin removal. These studies point towards an even greater reduction in mortality with further reduction in $\beta_2$-microglobulin.

SUMMARY OF THE INVENTION

As recognized by the present inventors, some important requirements for $\beta_2$-microglobulin or similar toxin removal systems are: (i) high resolution, (ii) minimal albumin loss, (iii) high-throughput and (iv) minimal hemocompatibility issues.

In light of the problems and deficiencies note above, a split thin-flow separations device can include a fluid channel having an inlet zone, an outlet zone, and a transport region between the inlet zone and outlet zone. The inlet zone includes a sample inlet and a carrier fluid inlet which are fluidly separated by an inlet splitter to minimize mixing of fluids from respective inlets in the inlet zone. The transport region can be a substantially open channel. Similar to the inlet zone, the outlet zone can include a sample outlet and a carrier outlet which are fluidly separated by an outlet splitter to segregate portions of a fluid into each of the two outlets as the fluid enters the outlet zone. At least one cross-flow inlet is also oriented along a wall of the fluid channel in the transport region. The cross-flow inlets are oriented to direct a cross-flow fluid into the transport region.

A method of separating components of a fluid using a split thin-flow process can include passing a sample fluid and a carrier fluid into a fluid channel under diffusional split-flow thin cell conditions. The sample fluid can include a first component which has a lower molecular weight than a second component in the sample fluid. The flow conditions can be maintained such that a first component of the sample fluid preferentially flows into a carrier fluid outlet. In addition, a cross-flow fluid can be injected transversely across the fluid channel under conditions sufficient to augment separation of the first component from the sample fluid while minimizing transfer of the second component into the carrier fluid outlet.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

BRIEF DESCRIPTION OF THE DRAWINGS

The present invention will become more fully apparent from the following description and appended claims, taken in conjunction with the accompanying drawings. Understanding that these drawings merely depict exemplary embodiments of the present invention and they are, therefore, not to be considered limiting of its scope. It will be readily appreciated that the components of the present invention, as generally described and illustrated in the figures herein, could be arranged, sized, and designed in a wide variety of different configurations. Nonetheless, the invention will be described and explained with additional specificity and detail through the use of the accompanying drawings in which:

DETAILED DESCRIPTION OF EXEMPLARY EMBODIMENTS

Figure 1:
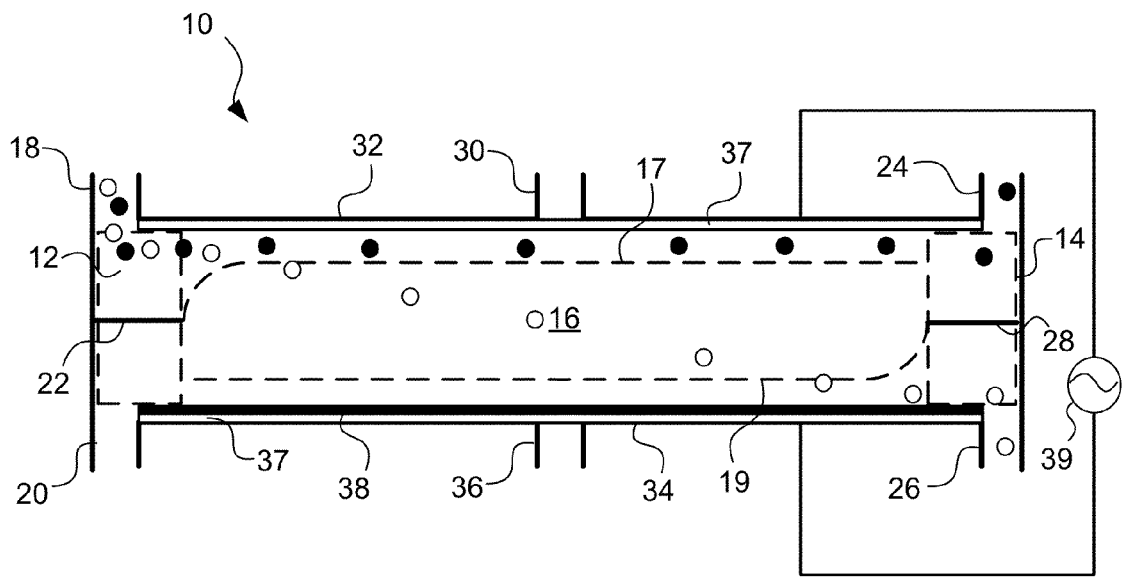
FIG. 1 is a side cross-sectional view of a split thin-flow separations device in accordance with one embodiment of the present invention. Note that the wall and splitter thicknesses are not to scale.

The following detailed description of exemplary embodiments of the invention makes reference to the accompanying drawings, which form a part hereof and in which are shown, by way of illustration, exemplary embodiments in which the invention may be practiced. While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

The following detailed description and exemplary embodiments of the invention will be best understood by reference to the accompanying drawings, wherein the elements and features of the invention are designated by numerals throughout.

DEFINITIONS

In describing and claiming the present invention, the following terminology will be used.

The singular forms "a," "an," and "the" include plural referents unless the context clearly dictates otherwise. Thus, for example, reference to "a channel" includes reference to one or more of such features and reference to "passing" refers to one or more such steps.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context. Adjacent also excludes an intermediate element between two adjacent structures. For example, two layers which are adjacent may have adhesive or other adhering material between them, but will not have a separate structural intermediate layer between them.

As used herein, "small proteins" refers to proteins which are categorized by the structural classification of proteins (SCOP) hierarchy. Non-limiting examples of typical small proteins includes $\beta_2$-microglobulin, insulin and Cystatin C.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Split Thin-Flow Separations with Cross-Flow

A novel cross-flow based split-flow lateral-transport thin separation (SPLITT) microsystems can be capable of high speed separations based on size or density of the sample. This approach uses a cross flow as the driving field.

FIG. 1 illustrates one design of a cross-flow device 10. A split thin-flow separations device can include a fluid channel having an inlet zone 12, an outlet zone 14, and a transport region 16 between the inlet zone and outlet zone. The inlet zone includes a sample inlet 18 and a carrier fluid inlet 20 which are fluidly separated by an inlet splitter 22 to minimize or prevent mixing of fluids from respective inlets in the inlet zone. The transport region can be a substantially open channel. This open channel can be free or substantially free of fixed members or other obstructions along the channel. Similar to the inlet zone, the outlet zone can include a sample outlet 24 and a carrier outlet 26 which are fluidly separated by an outlet splitter 28 to segregate portions of a fluid into each of the two outlets as the fluid enters the outlet zone.

At least one cross-flow inducer can be oriented along a wall of the fluid channel so as to form a cross-flow field. This can be accomplished by injecting a cross-flow fluid into the fluid channel and/or withdrawing cross-flow fluid from the channel. The cross-flow can be induced using a suitable mechanism such as a push-pull pump, syringe, microfluidic pump, valves, or other fluid flow control device. Thus, the cross-flow inducer can be a cross-flow inlet, a cross-flow outlet or both. Further, a common inducer can operate as either an inlet or an outlet depending on the operation of the associated fluid flow control device, e.g. pump. In one aspect, at least one cross-flow inlet 30 is also oriented along a wall of the fluid channel in the transport region 16. Cross-flow inlets are oriented to direct a cross-flow fluid into the transport region. In one aspect, the fluid channel walls can include a plurality of cross-flow inlets. The cross-flow split-flow-thin-cell is a continuous separation system that relies on cross-flow as a driving force to induce separation. The cross-flow is applied across the separation direction to either aid/reduce the sample movement across the thin separation lamina in split-flow-thin-cell.

As shown in FIG. 1, the device can include a thin ribbon like open fluid channel. Specifically, the transport region can be a rectangular ribbon channel having cross-flow inlet wall opposite a carrier wall and two side walls bridging the cross-flow inlet wall and carrier wall. More particularly, the two side walls can have a height substantially less than a width of each of the inlet wall and carrier wall, so as to form inlet fluid rich region proximate the cross-flow inlet wall and a carrier fluid rich region proximate the carrier wall.

Although the transport region 16 can have a constant cross-section, an asymmetrical cross-section can be useful. For example, the asymmetrical cross-section can have a decreasing channel width from the inlet zone 12 to the outlet zone 14. A reduction in cross-section helps to compensate for decrease in flow velocity along the length of the channel as cross-flow is continuously lost through the single porous wall of the channel.

Thus, depending on the cross-flow flowrate, the asymmetrical channel profile can be configured to maintain a constant (or substantially constant) flow velocity. Although the specific contours can vary, the ratio of inlet to outlet channel width in the open channel can vary from about 2 to about 8.

In another alternative aspect, the sample inlet 18, the sample outlet 24, and cross-flow inlets 30 are oriented on a common sample side 32 of the device as illustrated in FIG. 1. Similarly, the carrier fluid inlet 20 and carrier outlet 26 can be oriented on a carrier side 34 of the device opposite the sample side. Other orientations of inlets and outlets can be made as long as the split thin-flow region is maintained through the fluid channel. Although other dimensions can be suitable, in one aspect, the height can be from about 100 μm to about 1 mm, the width can be from about 2 mm to about 10 mm, and the fluid channel can have a length from about 4 cm to about 20 cm. The fluid channel can generally have a thin ribbon profile. For example, in some cases a ratio of the width to the height can be about 3:1 to about 20:1. For these dimensions, the sample fluid can generally have an inlet flow rate of about 0.5 ml/hr to about 5 ml/hr.

Although not required, at least one of the inlet zone and the outlet zone can also include a plurality of baffles extending from either or both sides of the corresponding splitter and which are oriented to inhibit turbulent mixing between fluid in the transport region adjacent the inlet zone or outlet zone. These baffles can be in the form of cylindrical columns, tapered columns, teardrop cross-section, or other shapes suitable to distribute flow and inhibit turbulent mixing such that substantially laminar flow can be maintained in the transport region by smoothing transition toward the open channel.

Figure 2:
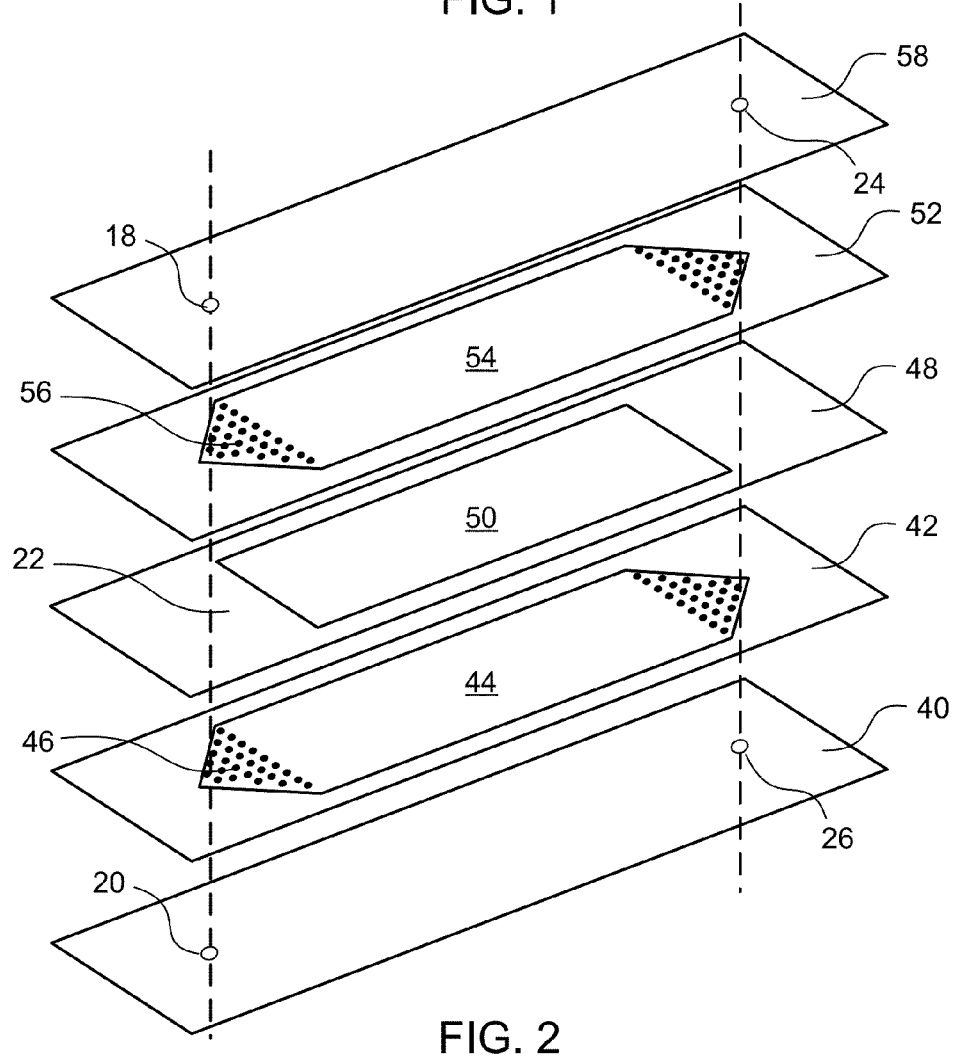
FIG. 2 is an exploded perspective view of the different layers of the diffusional-split thin-flow device in accordance with one embodiment of the present invention that includes a splitter layer between two flow channels with cylindrical columns in the triangular end sections.

In yet another aspect, the device can be formed as a layered structure as illustrated in FIG. 2. For example, a carrier wall plate 40 can form the carrier fluid inlet 20 and carrier fluid outlet 26 therein. A carrier side channel plate 42 can also be oriented adjacent the carrier wall plate having a first open region 44 and a first set of baffles 46. A splitter plate 48 can be oriented adjacent the carrier side channel plate and form the inlet splitter 22 and the outlet splitter 28 and a second open region 50 therebetween. A sample side channel plate 52 can be oriented adjacent the splitter plate having a third open region 54 and a second set of baffles 56. A sample wall plate 58 can have the sample inlet 18 and sample outlet 24 therein such that the first open region 44, the second open region 50 and the third open 54 region collectively form the fluid channel (item 16 in FIG. 1). In this configuration, two flow channels separated by a rectangular splitter in the middle constitute one design of such a device. Inclusion of a splitter dividing the two flow channels prevents unwanted mixing at the two inlets within the inlet zone and facilitates smooth transition of the sample fluid and carrier fluid into the transport region at the two outlets.

The cross-flow fluid can elute out with the carrier fluid, and optionally a portion with the sample fluid. Alternatively, or in addition, at least one cross-flow outlet 36 can be oriented along walls of the fluid channel, e.g. along the carrier wall plate 34, as illustrated in FIG. 1. Each of the cross-flow inlet and cross flow outlet can optionally include a frit layer 37 or other similar feature to distribute flow. Further, an optional membrane 38 can be placed along the carrier side wall and/or across the cross-flow outlet in order to block components from leaving out through the cross-flow outlet rather than the carrier fluid outlet.

The flow arrangement depicted in FIG. 1 is called a transport mode of separation. The dashed lines traversing the transport region 16 represent imaginary planes, i.e. an upper inlet splitting plane 17 (ISP) and a lower outlet splitting plane 19 (OSP). The transport region thickness or diffusion barrier distance between ISP and OSP can be controlled by changing the ratio between the inlet and outlet flow rates. For conventional operation, parameters such as diffusion barrier distance and time spent by the sample in the channel govern the separation of the samples with distinct diffusion coefficients or molecular weights. The thickness of the transport region can be compared to pore size of a membrane with conventional dialysis machines. Sample and buffer/carrier continuously enter through the separate inlets and the molecular weight distribution of the sample in each outlet can be controlled by varying the flow rates of each inlet and outlet. For example, a low molecular weight sample (e.g. Component B) enters the transport region faster and elutes more from the carrier outlet 26 and a high molecular weight sample (e.g. Component A) is much slower due to the lower diffusion coefficient and elutes preferentially from sample outlet 24.

By changing the thickness of the transport region and the time spent by the analyte in the channel, the molecular weight cut-off can be controlled. The dimensions of the channel can also be varied to effect residence time and diffusion length. For example, if a mixture of two different samples (such that sample A has a smaller diffusion coefficient than sample B) are passed through sample inlet 18 (as shown in FIG. 1) with flow rates maintained such that only some of Component B has enough time to diffuse across the transport region 16 and elute from carrier outlet 26. Under such conditions, only a very small amount of sample with lower diffusion coefficient particles will elute from the carrier outlet whereas a significant amount of Component B elutes from the carrier outlet. Thus, Component A has been purified substantially by preferential removal of Component B. Diffusional split thin-flow separation can be efficiently used to remove or purify proteins with a substantial difference in molecular weights very quickly even without the use of any external field. However, an external field can be optionally added to the diffusion process to allow for additional specificity and speed in some cases (e.g. where electrophoretic mobility differences are sufficiently high).

As mentioned, the component separation in the device can be driven by diffusion, electric field, magnetic field, gravity, centrifugal force, and/or a combination of these mechanisms. In these options, the driving force is molecular weight, electrophoretic mobility, density, magnetic permittivity, and size, respectively. Separation can be enhanced by applying an electric field across the channel height and can increase the separation power and increase the specificity of removed components (e.g. when multiple additional components are also present). Accordingly, in one aspect, an electric field source 39 can be electrically associated with the transport region 16 to allow an electric field to be applied across the fluid channel. The strength of the electric field can be adjusted based on the differences in electrophoretic mobilities of the components and associated fluid flow rates. The separation system 10 is also capable of continuous purification in an open-channel and does not require any membrane that would lead to biocompatibility or fouling issues. More specifically, neither the sample fluid nor carrier fluid pass through a membrane along the primary fluid flow through the device. Although some sample fluid or carrier fluid may mix with the cross flow fluid and exit via a cross-flow outlet 36. In other words, differences in diffusion of components is used rather than a membrane to segregate components from the sample fluid.

A wide variety of materials can be used to form the device walls, as long as such materials provide sufficient biocompatibility, durability, rigidity, etc. Suitable materials will depend on the application. For example, polyethylene materials may be suitable for single use low flow rate applications while unsuitable for long term applications. Similarly, although some metals can be used for industrial applications, some such metals may not provide biocompatibility for medical applications. Non-limiting examples of suitable materials for forming the fluid channel can include at least one of silicon, glass, metals, graphite, polymers such as MYLAR, polyethylene, PDMS and polyurethane, polymer tape, polymer films, and combinations thereof. In one aspect, the system can include fluidic channels and splitters made from polydimethyl siloxane (PDMS). To maintain an effective cross-flow across the fluid channel, a polyethylene frit can be used with an ultra filtration cellulose acetate membrane to prevent unwanted loss of sample particles (i.e. out the cross-flow outlet). Both frit and membrane can be located on either side of the fluidic channels that are sandwiched between two outer wall members such as Plexiglas® blocks. In one alternative aspect, the splitter can be formed of a biocompatible metallic material with high modulus, sufficient that there will be negligible bending under high flowrates, e.g. steel, brass, or any other thin metal sheet that can be suitably machined.

Fabrication

Although the device can be formed in any suitable manner, in one aspect, a unique approach can be taken. In particular, the system can be fabricated using PDMS (SYLGARD)-based multilayer soft lithography techniques. Molds for channel and splitter layers can be created by patterning tape using a knife plotter-based xurography technique. A splitter layer 48 is sandwiched between two layers of channel (42 and 52) as shown in FIG. 2. The design for xurography patterning is made such that baffles 46 and 56 can be formed as cylindrical columns in the triangular end sections of the channel. These baffle columns serve two purposes: (i) uniform distribution of the flow from point injection to the entire width of the channel section and (ii) mechanical support to an often flexible splitter layer. Thus, the columns can prevent undesirable collapsing or movement of the splitter layer. Each layer can have a corresponding thickness to form desired fluid channel inner dimensions. In one specific example, each plate can have a thickness of about 60 µm, although other thicknesses can be suitable. Generally, the total channel thickness (height) from the carrier side to the sample side is from about 100 µm to about 200 µm although other dimensions can also be suitable. The upper sample wall plate 58 and lower carrier wall plate 40 can be flat plates with holes drilled in therein corresponding to each of the inlets and outlets. Each layer can then be stacked in order as shown in FIG. 2. The layers can be held together through the use of an adhesive, gasket, and/or external clamping. In one aspect, the layers can be attached to one another using a thin adhesive tape such as, but not limited to, 25 µm tape (9019 from 3M). Other approaches to assembling the device can also be suitable such as (i) lamination, (ii) clamping, and (iii) thin layers can be molded and then cured together, etc.

The use of a microsystem fabricated using such rapid prototyping methods has unique advantages since a multitude of such split thin-flow fluid channels can be operated in a parallel fashion to satisfy high-throughput requirements associated with dialysis processes.

In another alternative aspect, interior walls, inlets and/or outlets can be optionally coated with an adsorption reducing coating in order to prevent or substantially reduce adsorption of proteins or other materials to these surfaces. Non-limiting examples of suitable adsorption reducing coating materials can include Pluronics®, silanes, self-assembled monolayers, and the like. Such materials can also serve to increase hydrophilicity of the walls, especially when the interior surfaces are PDMS, in order to improve flow uniformity through the channel. For example, a Pluronic solution can be pumped at a very slow flow rate (0.2 ml/hr) for 2 hours through the channel while the entire system is incubated at room temperature for 24 hours. Other similar flow, time and temperature conditions may also be used to achieve substantially the same coating results. In another example, when the materials are glass the glass surfaces can be treated with glow discharge plasma in order to reduce or eliminate bubble formation during use.

Operation and Applications

A method of separating components of a fluid using a split thin-flow process can include passing a sample fluid and a carrier fluid into a fluid channel under diffusional split-flow thin cell conditions. The sample fluid can include a first component which has a lower molecular weight than a second component in the sample fluid. The flow conditions can be maintained such that a first component of the sample fluid preferentially flows into a carrier fluid outlet. In addition, a cross-flow fluid can be injected transversely across the fluid channel under conditions sufficient to augment separation of the first component from the sample fluid while minimizing transfer of the second component into the carrier fluid outlet.

A wide variety of sample fluids can be treated such as, but not limited to, blood, nanoparticle suspensions, plasma, biological fluids, samples for environmental monitoring and clinical diagnostics. In one specific aspect, the sample fluid is blood. In this case, the first component can include at least one of $\beta_2$ microglobulin, parathyroid hormone, overdose drugs, small proteins, and other toxins. In one aspect, the first component can be a middle molecule such as, but are not limited to, $\beta_2$-microglobulin, para thyroid hormone, and p-cresol. When the sample fluid is blood, the second component is generally human serum albumin. The carrier fluid is generally phosphate buffered saline, although other fluids such as dialysate, isotonic buffers and the like can also be used. In the same manner, the cross-flow fluid is most often the same as the carrier fluid, although they can be differentiated to reduce concentration gradients between the cross-flow fluid and the sample fluid. In one alternative aspect, the carrier fluid and/or cross-flow fluid can be a separate phase from the sample fluid, e.g. immiscible. In another aspect, the carrier fluid and/or cross-flow fluid can have a substantially different density and/or viscosity from the sample fluid. In particular, in some circumstances the cross-flow fluid can differ in viscosity and density from the channel carrier fluid (e.g. combined sample fluid and carrier fluid).

Although operating conditions can vary depending on the particular application, the cross-flow fluid flow rate can be, but is not limited to, about 1 to about 10 times a combined inlet flow rate of the sample fluid and the carrier fluid. In one alternative, the cross-flow field can also be injected in reverse (e.g. from carrier side to sample side). This can be especially useful for dialysis related cases where recovery of 99% or more of albumin is desired. The reverse cross-flow field would ensure that not much albumin is lost and substantially the rest of the smaller toxins would diffuse out.

Depending on the type of components to be separated and fluid properties, the effectiveness of the thin-field flow can optionally include an applied electrical field. As mentioned, an electric field can be applied to change the rate of diffusion of either components. Typically, an applied electric field will change diffusion rates of different components differently such that the absolute difference between diffusion rates can be increased. In one particular aspect, an electric field can be applied across the fluid channel sufficient to reduce diffusion of the second component across the fluid channel. Although specific electric field strengths can depend on the fluids and configuration, electric fields from about 10000 V/m to about 80000 V/m can be useful. In this manner the second component is effectively held in the upper region close to the sample wall, as opposed to applying the electric field only to enhance diffusion of the first component across the channel, e.g. applying the electric field in reverse.

Optionally, or in addition, multiple separation units can be connected in series to further separate components in the sample fluid. In addition, to match the throughput required by dialysis machines or other applications, multiple systems can be connected in parallel to provide sufficient volumetric flow. In one aspect, a portion of the sample outlet can be recycled into the sample inlet stream so as to affect an increase in removal of the first component (e.g. component B).

When the sample fluid is blood, the method can further comprise performing hemodialysis on the blood prior to the step of passing the sample fluid through diffusional split-flow thin cell conditions. The sample fluid can also be returned to a patient subsequent to the diffusional split-flow thin cell conditions and injecting a cross-flow fluid.

The present invention can be effectively used to remove toxins such as beta-2-microglobulin ($\beta$2M) and parathyroid hormone that cannot be otherwise removed solely with present dialysis machines. The system can primarily expand the "diffusion length" in the channel while maintaining the small channel dimensions. Thus, the system is capable of conducting high resolution separation in real life samples such as blood plasma. It is also noted, that the diffusion coefficient of $\beta$2M is about 5 times more than albumin and the diffusivity of albumin is $0.61 \times 10^{-10}$ m$^2$/sec while $\beta$2M is $1.53 \times 10^{-10}$ m$^2$/sec. Therefore $\beta$2M is expected to diffuse more at the same flow rate conditions as albumin, if the concentrations of both proteins are the same. But, the typical concentration of albumin in uremic blood is close to 1000 times more than $\beta$2M. Such a steep concentration gradient creates a huge flux of albumin in comparison to $\beta$2M and hence, a higher loss from the sample stream, as the driving force is 200 times more for albumin. For this reason, the separation resolution is governed by relative concentration dependent convective dispersion and not just the difference in diffusion coefficients or molecular weights of the proteins and warrants very different operating conditions compared to conventional SPLITT operation. For example, generally, higher carrier flow rates and higher overall flow rates tend to keep the albumin on the sample side while still allowing diffusion of the $\beta$2M to the carrier side, etc. Although other conditions can be favorable, as a general guideline, a carrier flow rate to sample flow rate ratio of about 2:1 to about 4:1 can be desirable.

One consideration in blood filtering (depending on the flow rate protocol being used) is a potential sample dilution that would require a post-treatment unit to remove excess water from the outlet stream. Thus, in some embodiments, a water removal unit such as a membrane-based reverse osmosis type system that allows water to escape and prevents important proteins from diffusing out, can be fluidly connected downstream of the split thin-flow separations device. In addition, this set of methods is particularly suited for soluble toxin separations. Any undesirable moiety bound to proteins or cells would require special operating conditions, but it should be noted that most of the toxins that are removed by the kidney itself are essentially water soluble. Such cases can be addressed by changes in buffer conditions and/or separate affinity-based units.

The device also has applications in a variety of other areas. For example, toxin removal to aid hemodialysis, drug removal in patients ailing from overdosing, protein and other biomolecule processing, nanoparticle purification and characterization, blood toxin removal, drug screening, bio fuel production and purification, environmental monitoring, and nanoparticle purification (including increasing monodispersity).

One advantage of a split thin-flow device over membrane-based systems stems from the absence of a solid membrane to induce filtration, thus preventing the potential complications associated with fouling or biocompatibility. Additionally, the separation process is very rapid in proportion to the small diffusion barrier distance (along the channel height direction). Miniaturization of the system can further reduce the separation time as the diffusion lengths are even smaller for microsystems. Another practical advantage of miniaturization of these systems is the reduction in sample and carrier solution volumes. The width of the fluid channel being operated in continuous mode can be increased without sacrificing separation power or any edge effects which are commonly found in field-flow fractionation systems of the prior art.

As a general guideline for operating parameters, one goal of diffusional operation when used for blood purification is to remove unwanted toxins and to keep desired proteins such as HSA intact. In order to optimize the operation of the diffusional system, a proper understanding of the effect of each control variable, such as: total flow rate (flowrate through sample inlet+flowrate through carrier inlet), inlet flow rate ratio (sample inlet flow rate/total flow rate, referred as the inlet ratio), outlet flowrate ratio (sample outlet flow rate/total flow rate, referred as outlet ratio), and diffusion coefficient, on the selectivity of the samples being purified is desirable. As the total flowrate controls the residence time of the sample in the channel, the extent of diffusion across the transport region can be altered with a proper control of the total flowrate. Additionally, if the inlet ratio is decreased and/or outlet ratio is increased, the width of the transport region increases, which means that the sample has to migrate farther to reach the OSP. By adjusting the flowrates, the cut off diffusivity for particles can be adjusted, so only particles with higher diffusivity than this cut off limit, can elute out from carrier outlet.

In order to monitor performance and concentration of components in the outlets, outlet fluid can be directed through a flow cell of a UV detector (e.g. Model 520 UV/Vis detector from ESA Inc. is one suitable example). The area under the elution peaks can be determined using PeakFit Software, Systat Software Inc., CA and used to calculate the fractional retrieval rate $F_{(a')}$ for each protein eluting from the outlet $V_{(a')}$ as $$[F_{(a')}] = \frac{P_{(a')} \cdot V_{(a')}}{P_{(a')} \cdot V_{(a')} + P_{(b')} \cdot V_{(b')}}, \quad (1)$$

where, $P_{(a')}$ and $P_{(b')}$ are the peak areas under the elution curves for outlets a' and b' respectively. In the following discussion, sample inlet 18 is a, sample outlet 24 is a', carrier inlet 20 is b, and carrier outlet 26 is b'.

Samples could be collected from only one outlet and the concentration of the protein from the other outlet can be calculated based on the concentrations of the initial sample and the collected fraction by setting up a material balance equation.

For example, if protein is collected from the outlet $V_{(a')}$ and its concentration ($[C_{(a')}]$) is known after the immunoassay, then the concentration of protein ($[C_{(b')}]$) eluting from $V_{(b')}$ can be calculated as $$[C_{(b')}] = \frac{[C_{(a)}] \cdot V_{(a)} - [C_{(a')}] \cdot V_{(a')}}{V_{(b')}}, \quad (2)$$

where, $[C_{(a)}]$ and $V_{(a)}$ are the concentrations and flow rates of the inlet stream respectively.

Thus, the fraction of protein from any outlet can be collected from the mass balance of the eluting streams as $$[F_{(b')}] = \frac{[C_{(b')}] \cdot V_{(b')}}{[C_{(a')}] \cdot V_{(a')} - [C_{(b')}] \cdot V_{(b')}}, \quad (3)$$

Equations 1-3 apply to conventional SPLITT but similar balances can be derived which include cross-flow volumes. Alternatively, samples can be collected from both outlets and corresponding fractions can be determined directly by measurement.

EXAMPLES

Example 1

Polystyrene particles of size 490 nm were injected in a single dosage for system characterization. The flow rates used for cross-flow and channel flow (sample and carrier inlets combined) were 1 ml/hr and 2 ml/hr, respectively. The outlets of the SPLITT were connected to two UV/VIS detectors to measure the particle fractions in each stream. The absorption peaks detected by the detectors are obtained at both the outlets. Initial results showed that the system is capable of retaining most of the polystyrene particles.

Example 2

Figure 3:
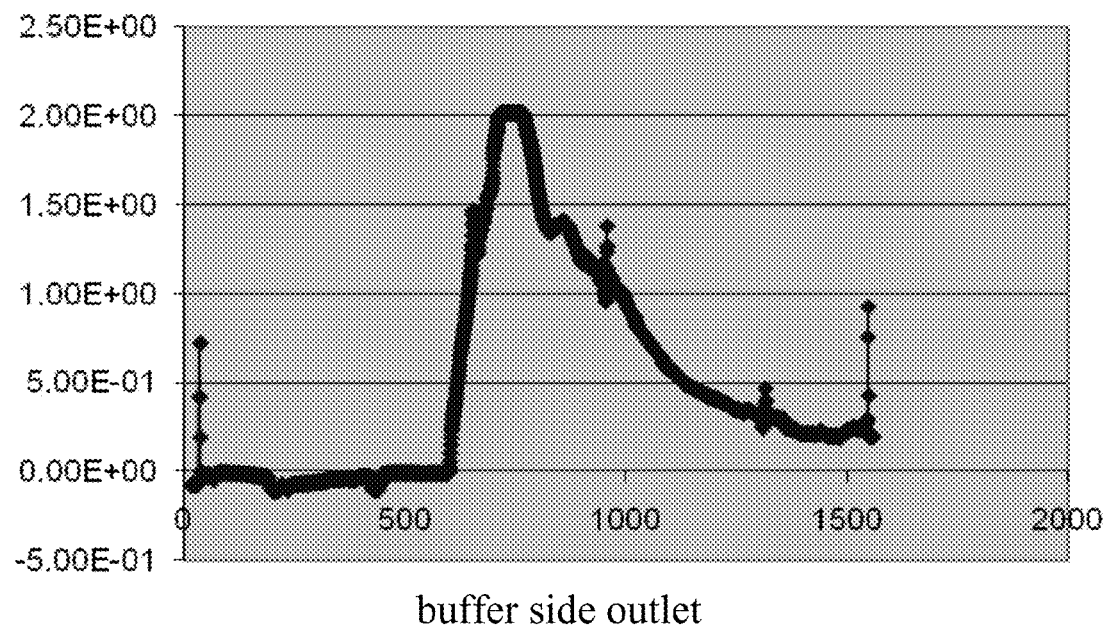
FIG. 3 is a graph of UV absorption versus time for the buffer side outlet in accordance with one embodiment of the present invention.
Figure 4:
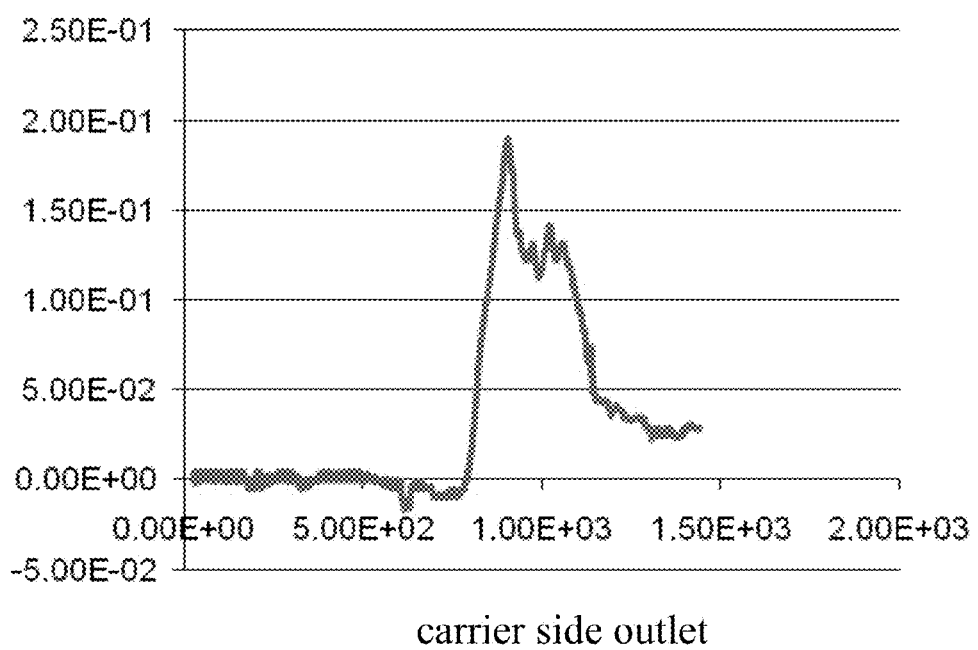
FIG. 4 is a graph of UV absorption versus time for the sample side outlet in accordance with one embodiment of the present invention.

The channel dimensions were 7 cm length, 5 mm width and 0.5 mm channel height. Polystyrene particles of 209 nm diameter were tested and elution of the particles was detected at two outlets, outlet 'a' (sample) and outlet 'b' (carrier) by the detectors. The flow rates used were 1 ml/hr for the perpendicular or cross flow and 2 ml/hr for the lateral or normal flow. The absorption peaks detected by the detectors are obtained at both the outlets as shown in FIG. 3 and FIG. 4. At the outlet 'a' particles were collected at approximately 740 seconds and at the outlet 'b' approximately at 800 seconds. The cross-flow field resulted in more than 70% particles crossing the transport region and eluting from the buffer side outlet.

Example 3

Glass plates of 6.4 mm thickness were used as the substrate. Inlet and outlet ports, 34 cm apart were created in the substrate with a silicon carbide drill bit of 1.5875 millimeters diameter. The separation device consisted of two flow channels that are separated by a rectangular splitter to avoid mixing and recirculation at the channel ends as shown in FIG. 2 (not to scale).

A Mylar sheet of 0.1 mm thickness and a polyethylene sheet of 0.25 mm thickness were patterned using a knife plotter (Graphtec America, FC 5100-75) (xurography), to obtain channels and the splitter respectively. The overall length of the splitting region was 20 cm. The channels were attached to either sides of the splitter using 25 μm thick tapes with adhesive on both sides (9019, 3M) to facilitate proper alignment of the laminates. The total thickness of the fluid channel was 0.5 mm. To improve the flow distribution, small Mylar structures (three parallel bars along the flow channel axis at each of the inlet zone and outlet zone) were attached to the splitter using double side tape at the channel ends. Another purpose of these structures was to provide mechanical support to the polyethylene splitter and prevent buckling due to the difference in sample side and carrier side flow rates.

Prior to assembly, the glass substrates were cleaned with piranha etching solution and washed with DI water. The glass substrates were also treated with glow discharge plasma (Enercon Industries Corp., LM4243-05) to make them hydrophilic which in turn facilitate easy removal of bubbles during experiments. The channels without glow discharge showed only partial filling of the channel with a potential for decreased efficiency.

The channel was assembled by placing the channel laminates between glass substrates and fastening the resultant assembly between two plexiglass blocks with 16 bolts with a torque wrench (PROTO-J6177F, 30 Kg-cm). Standard fluidics fittings and tubing was used to complete the flow assembly for the cross-flow diffusional SPLITT system.

The experimental setup for the flow arrangement included two syringe pumps in infusion mode (KDS 100, KD Scientific) which were used to pump carrier and particles solution through the sample inlet and the carrier inlet. Outlets of the SPLITT system were connected to two identical UV detectors (1.2 µL Model 520 UV/VIS, ESA Inc) operating at 200 nm wavelength with 7 cm long and 0.030 inch inside diameter tubing. One more syringe pump (KDS 200), in withdraw mode, was connected to the sample outlet to control the outlet flowrates with the other outlet left open to the atmosphere. A microliter syringe (777, Hamilton) was used to inject sample with an in-line T-injector. The fraction collected from the outlets was determined based on the area under the absorbance peak (Peakfit Software) obtained for the respective elutions.

After assembling the SPLITT system, a 50 mM pluronic solution (BASF, Material 30085093) was continuously passed through the system at 0.1 ml/min for 24 hours and then incubated at room temperature for 24 hours. Pluronic treatment helps reduce undesirable protein adsorption on the channel and tubing walls.

An aqueous PBS buffer solution (pH 7.4) was used as the carrier fluid for all the runs described in this example. The HSA (A9771, Sigma) concentration used for these experiments was 3 mg/ml (PBS buffer). Similarly, 132-Microglobulin (M4890, Sigma-Aldrich) and parathyroid hormone (P3796, sigma) solutions were prepared at 3 mg/ml concentrations. The HSA concentration for the continuous purification experiments was 0.5 mg/ml.

Results and Discussion

As the diffusivities of $\beta 2M$ and PTH are higher than HSA, the total flowrate for the diffusional SPLITT was chosen so that a minimum amount of HSA diffuses across the transport region and elutes out of the waste outlet (carrier outlet). Unlike the H-filter, the amount of time spent by sample in the SPLITT channel is an influential parameter for diffusional SPLITT. If the total flow rate is too slow, then too much HSA is able to diffuse into the waste carrier outlet. In such a scenario, the ratio of HSA obtained from outlets will always be equal to ratio of outlet flow rates as it gets uniformly dispersed across the SPLITT channel. In contrast, if the total flow rate is extremely high it is possible to collect all HSA through the sample outlet. However, this can also limit the removal of smaller proteins because there will not be enough time for any sample to diffuse across the transport region. For this reason, the experiments were designed to optimize total flow rate so that most of the HSA elutes out of the sample outlet with a significant proportion of the other molecules eluting out of the waste carrier outlet.

Figure 5:
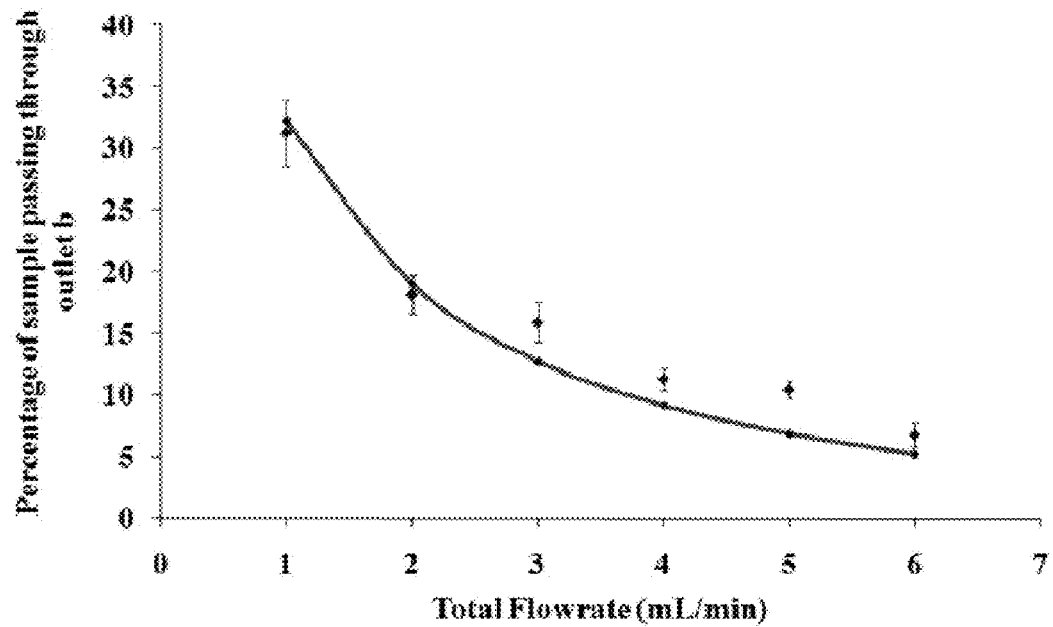
FIG. 5 is a graph of percentage of HSA lost through the carrier outlet and total flow rate (inlet ratio: 3/10; outlet ratio: 1/2).

The area under the absorbance peaks measured from detectors connected to each of the sample outlet and the carrier outlet represent the number of particles that elute from a specific outlet. FIG. 5 is a plot of the percentage of HSA eluting from the carrier outlet for different total flow rate runs. The ratio of inlet flow rates (sample inlet/carrier inlet) is kept constant at 3:7 and outlet flow rates are kept equal. In these experiments, the distance between ISP and OSP, known as the transport region will remain constant even with a varying total flow rate. Only the time for the sample to diffuse across the transport region will be changing.

At smaller total flow rates, HSA disperses across the entire transport region of the channel. Hence, the absorbance ratios will be closer to 0.5 (50%). As the total flow rate is increased, the percentage of HSA diffusing through transport region and eluting from the carrier outlet is decreased. This improvement with an increase in total flow rates can be used to increase the overall throughput, if required. Experiments were repeated more than 3 times to check the repeatability of the results. The maximum deviation found in results was less than 15%. After analyzing the initial results, the total flow rate of 4 ml/min was chosen as only 11% of the total HSA was lost through waste carrier outlet. This loss can be further reduced by increasing the width of the transport region (but at a cost of reduction in the efficiency of the system for removing smaller molecules), which in turn can easily be done by varying the inlet ratio or outlet ratio. The solid line in FIG. 5 represents the data obtained from numerical simulations of this system. FIG. 5 shows that simulation results and experimental results match very well. For larger total flow rates, the experimental values for percentage of particles eluting out of the carrier outlet were higher than the values obtained in the simulations. These deviations are a result of mixing and other instrumentation problems, which are not considered in the numerical model as they vary from one device to another.

Effect of Inlet Flow Rate Ratio

Figure 6:
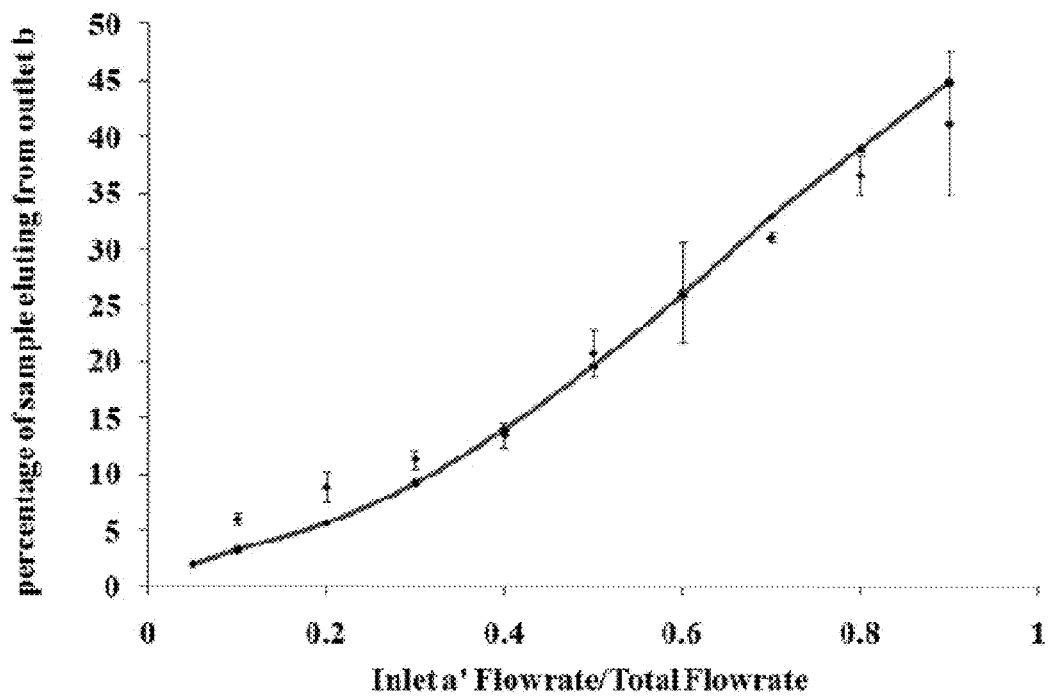
FIG. 6 is a graph of percentage of HSA lost through the carrier outlet for a variety of inlet ratios (Total flow rate: 4 ml/min; outlet ratio: 1/2).

Varying the inlet flow rates, while keeping outlet flow rates and the total flow rate constant, will change the thickness of the transport region. The resolution of separation is dependent on the width of the transport region; therefore, optimization of inlet flowrates can affect purification results. FIG. 6 is a plot of inlet ratio and percentage of particles eluting out from the carrier outlet.

For small inlet ratio values, the width of the transport region will be large; therefore, small inlet ratio values with relatively high flow rates (4 ml/min) will cause little amount of sample to elute out of the carrier outlet. When the inlet ratio is equal to 0.5, the ISP and OSP coincide with each other and there will be no transport region. When this ratio is more than 0.5, even if the sample does not diffuse at all, some of the sample will still elute from the carrier outlet as the ISP stretches into the OSP. The maximum experimental error found in these experiments was less than 9%.

The thicker line in the plot represents the modeling results. From FIG. 6, when the inlet ratio becomes large the modeling results do not match the experimental results. At these very low flow rates, there is a higher probability of some destabilization of the inlet flow, causing mixing and elution from the carrier outlet. During experiments, it has also been observed that the percentage of particles reaching the carrier outlet are not reduced to less than 5% due to instrumentation errors (which may be correctable with better instrument design). For very small flow rates, experimental results actually started reversing i.e., more particles eluted out from the carrier outlet. Modeling results did not confirm this trend, meaning that there are unknown wall or mixing effects, which are forcing particles away from the wall.

Effect of Outlet Flow Rate Ratio

Figure 7:
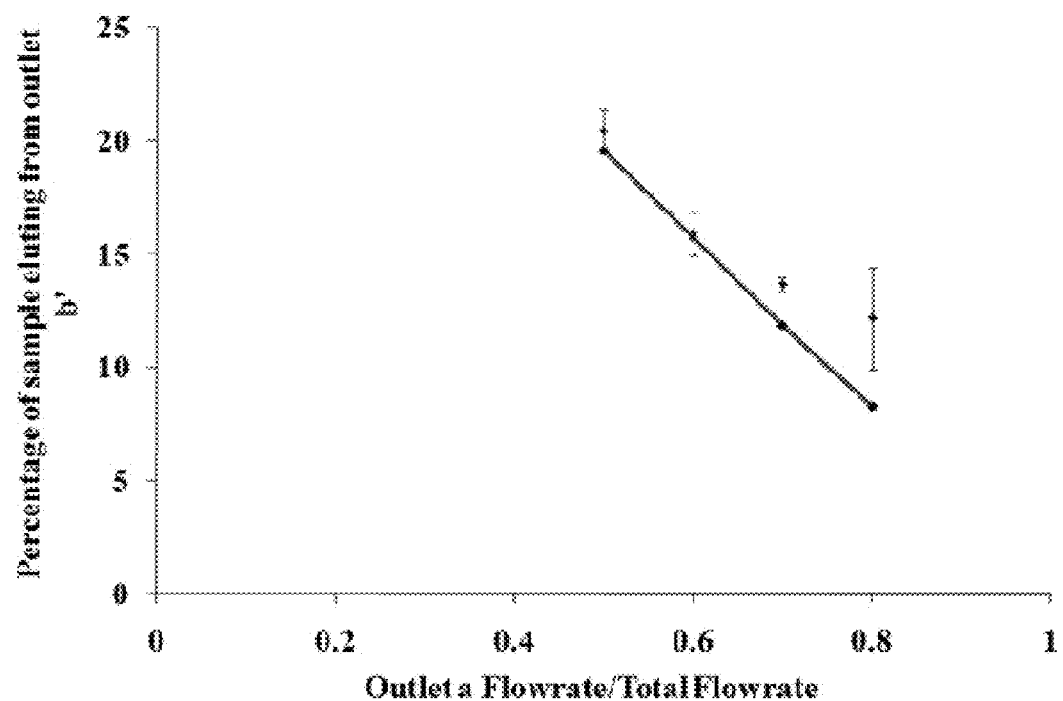
FIG. 7 is a graph of percentage of HSA lost through the carrier outlet for a variety of outlet ratios (Total flowrate: 4 ml/min; inlet ratio: 1/2).

Varying outlet flow rates while keeping inlet flow rates equal and constant can also modify the transport region. FIG. 7 is a plot which shows the effect of outlet ratio on the percentage of particles eluting from the carrier outlet.

If the outlet ratio is increased, the width of the transport region increases, which causes less sample to elute from the carrier outlet. Hence, HSA can be forced to pass through the sample outlet by using large outlet ratio values. These results match positively with the modeling results which are represented as a solid curve in FIG. 7.

Continuous Small Protein Removal

Figure 8:
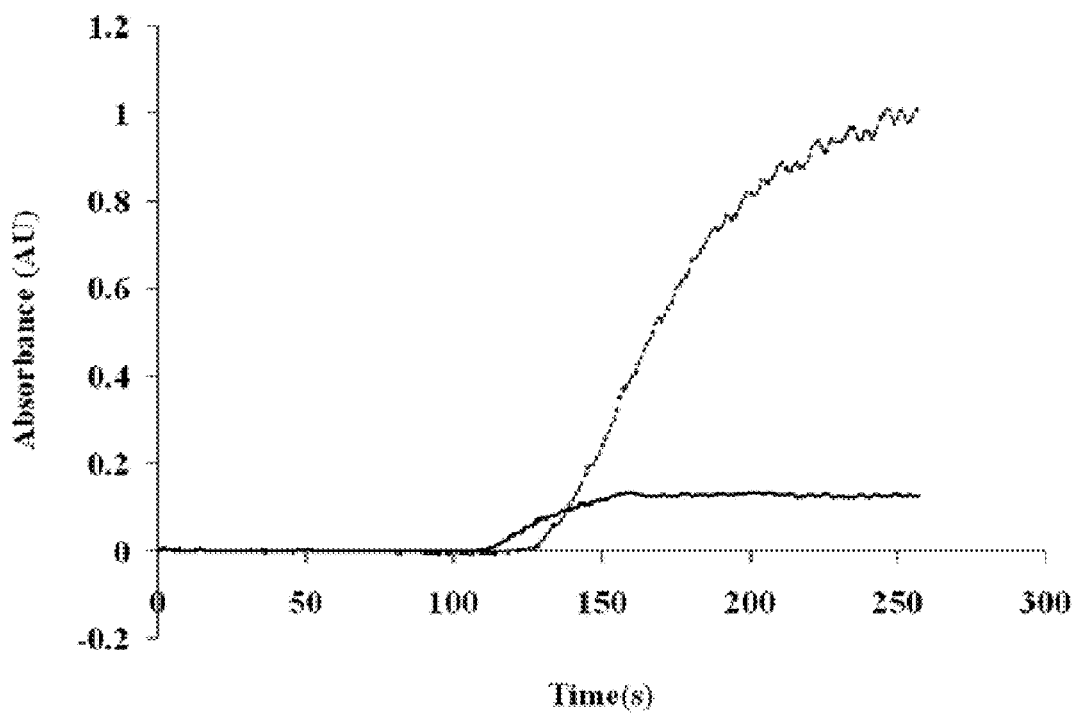
FIG. 8 is a graph of detector responses from the sample and carrier outlets (Total flowrate: 4 ml/min; inlet ratio: 1/10; outlet ratio: 1/2).

Experiments conducted by passing protein solutions continuously through the sample inlet, showed similar results as found in previous experiments when a concentrated sample is injected. FIG. 8 shows the responses of detectors connected to the sample outlet and the carrier outlet. This experiment was conducted with sample inlet, carrier inlet, sample outlet and carrier outlet flow rates at 0.4 ml/min 3.6 ml/min, 2 ml/min and 2 ml/min respectively. HSA concentration was 0.5 mg/ml.

This result clearly demonstrates that the detector response of the sample outlet was almost 9 times greater than the carrier outlet. This closely matches with the experimental results obtained using sequential sample injection. Thus, the percentage of HSA restored from the sample outlet was 90%.

Parathyroid Hormone (PTH) and $\beta_2$-Microglobulin ($\beta 2M$)

Continuous flow experiments similar to the ones used for HSA were also run using PTH and $\beta 2M$ with the same operating parameters as used for the HSA experiment. The percentage of $\beta 2M$ and PTH collected through the carrier outlet were 24.6% and 18.8%; Hence, significantly large amount of smaller molecules can be collected at the carrier outlet than HSA for the same operating conditions. In the present case, nearly triple the percentage of $\beta 2M$ and double the percentage of PTH was removed compared to HSA. These results suggest that diffusional SPLITT systems can be useful in eliminating dangerous toxins such as $\beta 2M$ and PTH without losing a significant amount of HSA.

Example 4

An asymmetrical cross flow based SPLITT system has been used to purify 120, 220 nm polystyrene nanoparticles and Bovine Serum Albumin (BSA) in less than 15 minutes.

Figure 9:
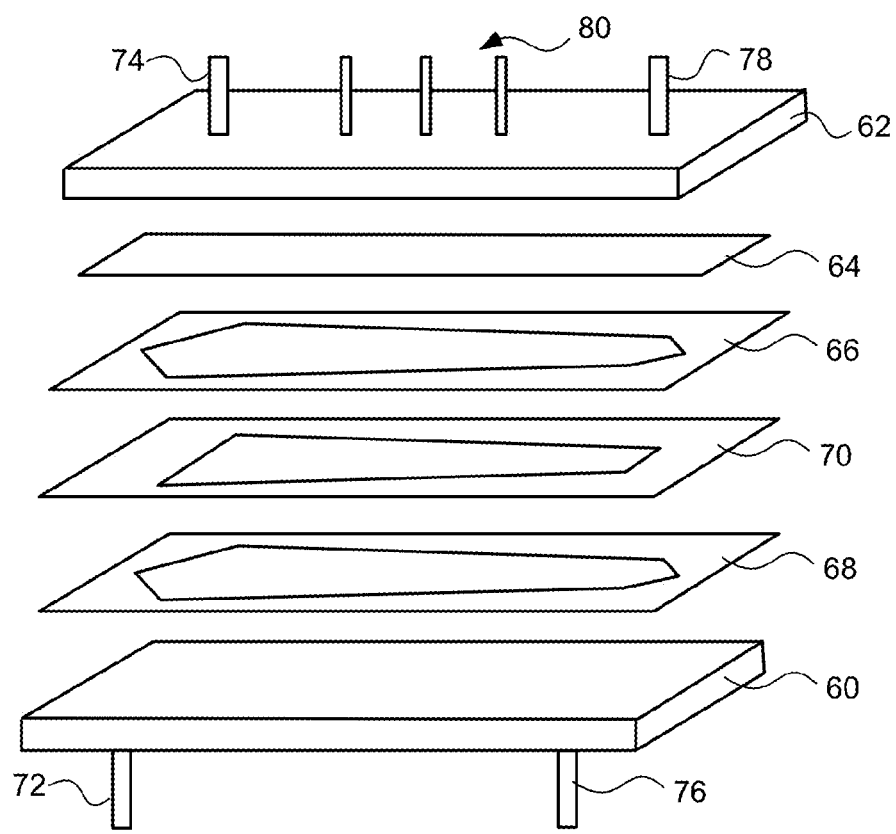
FIG. 9 is an exploded perspective view of an asymmetrical split thin-flow device in accordance with another embodiment of the present invention.
Figure 10:
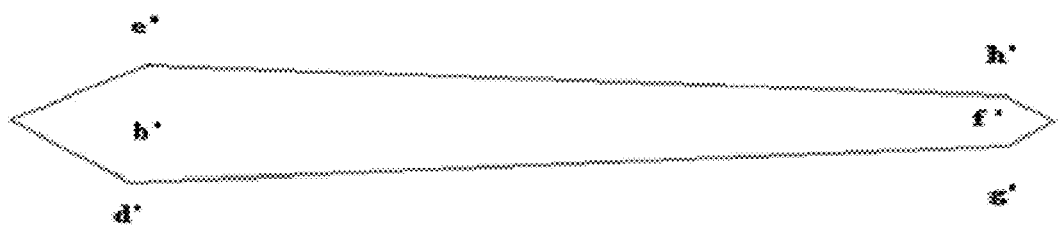
FIG. 10 is a top plan view of asymmetrical openings for the open channel in accordance with one aspect.
Figure 11:
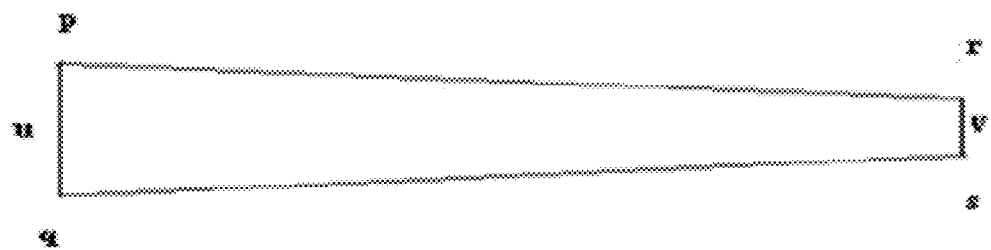
FIG. 11 is a top plan view of an asymmetrical opening for a splitter plate in accordance with another aspect of the present invention.

Components of the asymmetric SPLITT system include a glass block 60, frit block 62, semi permeable membrane 64, two asymmetrical microfluidic channels 66 and 68, and one trapezoidal splitter 70, as shown in FIG. 9. Similar to the configuration described in connection with FIG. 2, this configuration includes a sample inlet 72, a carrier inlet 74, a sample outlet 76 and a carrier outlet 78. This device also includes three cross-flow outlets 80. One of the fluidic channels is made of double sided tape of thickness 50 µm and the other one is a thin PDMS layer coated on double sided tape of thickness 100 µm. The separation spacer is made of a thin Mylar film of 125 µm thick to form the splitter. The channel-splitter assembly is sandwiched between the two supporting blocks. FIG. 10 and FIG. 11 shows the dimensions of the separation channel and splitter, respectively, where a-b=7 cm; a-c=1 cm; a-d=1.059 cm; d-e=0.7 cm; b-f=0.4 cm; g-h=0.35 cm and h-b=0.43 cm and p-q=0.7 cm; r-s=0.35 cm; u-v=5.6 cm. One side of the flow unit has a porous polystyrene frit block 62 that allows for cross-flow in or out of the channel. The frit membrane was a PM0530 microporous PTFE membrane having a pore size of 5-9 µm, porosity of 40-45%, and a thickness of 3.0±0.25 mm. This frit also acts as one of the supporting blocks for the channel-splitter assembly and a glass slide 60 on the other side acts as other supporting block. These blocks provide mechanical stability to the SPLITT system. An ultra filtration membrane 64 of 10 k molecular weight cutoff was used. Push-pull syringe pumps were used for driving the buffer liquid.

Figure 12:
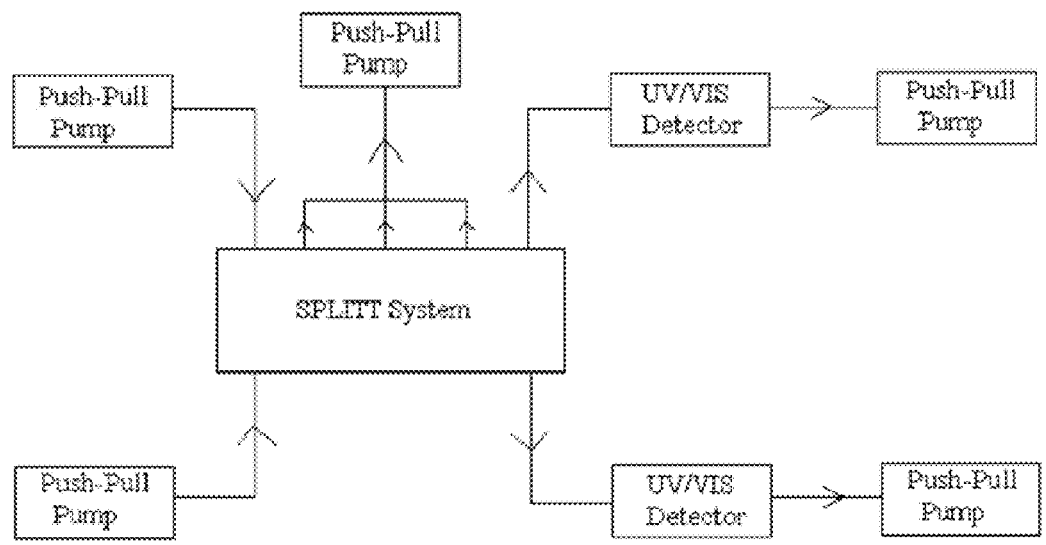
FIG. 12 is a schematic diagram of a system incorporating the split thin-flow devices in accordance with one aspect of the present invention.

The cross-flow field was applied in the transverse direction of the channel. The direction of the field applied was outwards. This cross-flow field was achieved using a push-pull pump which draws the solvent or buffer solution out of the system through the porous frit. The cross-flow field exerts equal force of flow stream and transport to all the particles along its path towards the accumulation wall. A t-injector and microliter syringe was used to inject the sample for preliminary characterization of the system and standard fittings were used to connect the microsystem and the syringe pumps. Most of the sample particles eluted from the sample outlet and only the smaller particles in a given size range (larger than the pores of membrane wall) diffuse and cross the inlet splitting plane and were collected at the carrier outlet. A schematic of the test setup system is shown in FIG. 12.

An amount of 10 µl of polystyrene particles of size 120, 220 nm and BSA were injected for system characterization. The outlets of the separation device were connected to two UV/VIS detectors to measure the particle fractions in each stream. The separation peaks observed by the detectors confirmed that the system is capable of purifying and separating both nanoparticles and proteins.

Case 1

DI water mixed with FL70 was used as carrier fluid. FL70 was used in order to avoid clogging of any particles inside the channel. The carrier fluid was made to pass into the system using push-pull pumps. Also, the particles were injected into the inlet stream from the sample inlet. A 10 µl volume of 1 mg/ml concentration Bovine Serum Albumin protein particles were used as sample. The cross-flow was used to draw the carrier solution from the system out through the porous frit and was maintained at 2 ml/hr flowrate. The cross-flow was used to force the particles towards the carrier side wall. The flow rates of sample and carrier inlets were maintained at 3 ml/hr and 1 ml/hr, respectively. Carrier outlets and sample outlet were the outlets connected to the UV detectors and then to push pull pumps which drew the carrier solution and particles out of the system. Both the outlets were maintained at a flowrate of 1 ml/hr.

Figure 13:
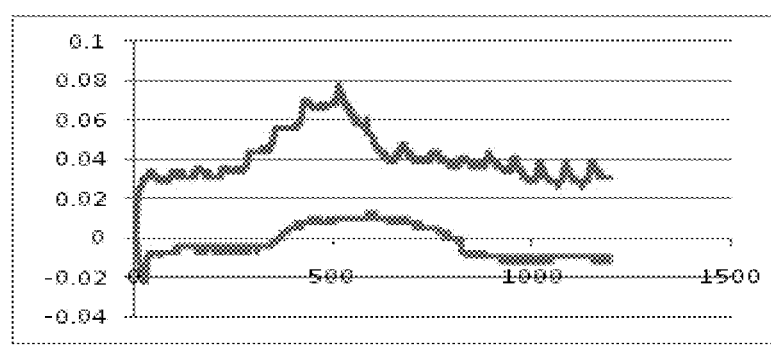
FIG. 13 is a graph of absorbance peaks for bovine serum albumin at each of the carrier and sample outlets for case 1.

FIG. 13 shows the absorbance peaks detected by the UV detectors at the two outlets. The absorbance peaks at carrier outlet and sample outlet was 0.068 AU and 0.013 AU, respectively. It was observed from FIG. 13 that the amount of particles eluted from the carrier outlet was slightly more than that at the sample outlet. The absorbance of peaks started 235 seconds for carrier outlet and 309 seconds for sample outlet. A 3 ml/hr flowrate at sample inlet was more than that of the carrier inlet which was 1 ml/hr. This higher flow rate makes the effective path of the particles towards the carrier wall and the cross-flow of 2 ml/hr pushes the particles that are in their laminar path further towards the carrier wall making the particles to come the carrier outlet and the remaining particles follow their own laminar path and elute from the sample outlet. The number of particles and the magnitude of absorbance show that a higher number of particles eluted from the carrier outlet than from the sample outlet.

Case 2

Figure 14:
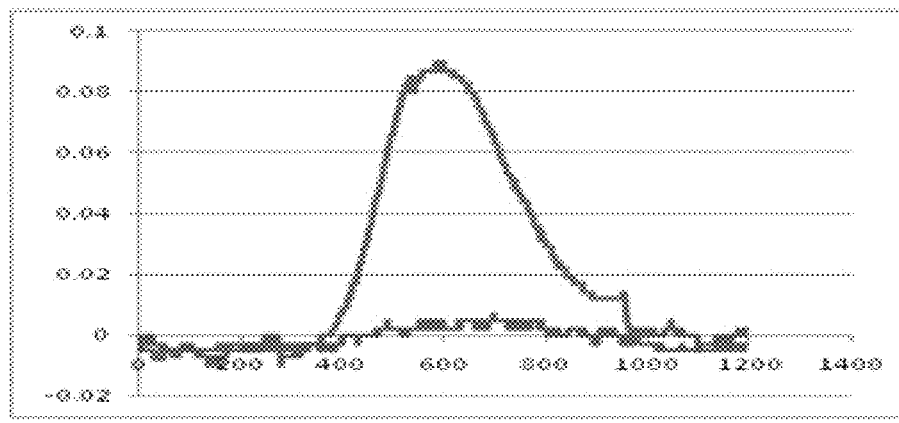
FIG. 14 is a graph of absorbance peaks for bovine serum albumin at each of the carrier and sample outlets for case 2.

Inlet flow rates for the SPLITT system were set at 3 ml/hr and 1 ml/hr at inlets a, b respectively using push-pull pumps with a cross-flow flowrate of 2 ml/hr. The resulting outlet flowrates were 1 ml/hr from each outlet. FIG. 14 shows the absorbance peaks of albumin particles of the same volume and concentration used for the first set of experiments. The magnitudes of the absorbance were 0.085 AU at the sample outlet and 0.005 AU at the carrier outlet. It was observed that most of the particles eluted from the sample outlet compared to the carrier outlet. The higher flowrate of the carrier inlet pushed the particles towards the sample wall. The cross-flow also forced the particles towards the carrier wall, but the effect of higher inlet flowrate at the carrier side was more compared to the cross flow effect. Hence most of the particles eluted from the sample outlet. The absorbance peaks confirms this observation.

Case 3

Figure 15:
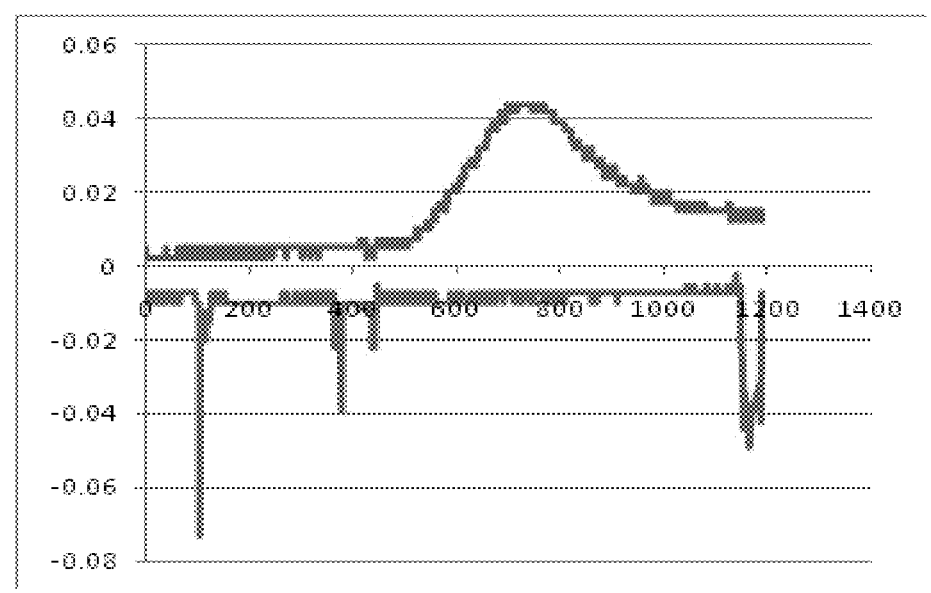
FIG. 15 is a graph of absorbance peaks for bovine serum albumin at each of the carrier and sample outlets for case 3.

The carrier solution used was deionized water mixed with FL 70. FL 70 avoids clogging of the particles inside the separation channel. The sample used for is 10 µl mg/ml Bovine Serum Albumin. The particles were injected from the same side as that of the cross-flow field. The carrier inlet flowrate was 1 ml/hr, the sample inlet flowrate was 3 ml/hr and the cross-flow flowrate was 2 ml/hr. Again, each of the outlets had a flowrate of 1 ml/hr. FIG. 15 shows the absorbance peak detected by the UV detectors at each of the outlets.

Because of the differential inlet flowrates the path of the fluid inside the channel was affected. The three times higher flowrate at the sample inlet forced the laminar path of the carrier fluid towards the carrier wall. Also the 2 ml/hr cross-flow field used was drawing the fluid out from the porous frit membrane and assisted in forcing the particles towards the carrier wall. Hence all the particles that were injected into the channel were eluted from the carrier outlet. It was observed from the results that both differential flowrate and the cross-flow acting dominated the rate of diffusion of the polystyrene particles. A similar effect was demonstrated from the other absorbance peaks for 130 nm polystyrene particles and Bovine Serum Albumin particles.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A split thin-flow separations device, comprising:
   a) a fluid channel having an inlet zone, an outlet zone, and a transport region between the inlet zone and outlet zone, said inlet zone including a sample inlet and a carrier fluid inlet which are fluidly separated by an inlet splitter to minimize mixing of fluids from respective inlets in the inlet zone, said transport region being a substantially open rectangular ribbon channel having a sample wall opposite a carrier wall and two side walls bridging the sample wall and carrier wall, said two side walls having a height substantially less than a width of each of the sample wall and carrier wall, so as to form an inlet fluid rich region proximate the sample inlet wall and a carrier fluid rich region proximate the carrier wall, and said outlet zone including a sample outlet and a carrier outlet which are fluidly separated by an outlet splitter to segregate portions of a fluid into each of the two outlets as the fluid enters the outlet zone; and
   b) at least one cross-flow inducer along a wall of the fluid channel in the transport region, said at least one cross-flow inducer is oriented to direct a cross-flow fluid into the transport region.

2. The device of claim 1, wherein the sample inlet, the sample outlet, and at least one cross-flow inducer are oriented on a sample side of the device.

3. The device of claim 2, wherein the carrier fluid inlet and carrier outlet are oriented on a carrier side of the device opposite the sample side.

4. The device of claim 1, wherein a ratio of the width to the height is about 3:1 to about 20:1.

5. The device of claim 1, wherein the transport region has an asymmetrical cross-section.

6. The device of claim 5, wherein the asymmetrical cross-section has a decreasing channel width from the inlet zone to the outlet zone.

7. The device of claim 1, wherein at least one of the inlet zone and the outlet zone include a plurality of baffles extending from either or both sides of the corresponding splitter and which are oriented to inhibit turbulent mixing between fluid in the transport region adjacent the inlet zone or outlet zone.

8. The device of claim 1, wherein the device is formed as a layered structure including:
   a) a carrier wall plate having the carrier fluid inlet and carrier fluid outlet therein;
   b) a carrier side channel plate oriented adjacent the carrier wall plate having a first open region;
   c) a splitter plate oriented adjacent the carrier side channel plate and forming the inlet splitter and the outlet splitter and a second open region there between;
   d) a sample side channel plate oriented adjacent the splitter plate having a third open region; and
   e) a sample wall plate having the sample inlet and sample outlet therein such that the first open region, the second open region and the third open region collectively form the fluid channel.

9. The device of claim 1, further comprising an electric field source electrically associated with the fluid channel to allow an electric field to be applied across the fluid channel.

10. A method of separating components of a fluid using a split thin-flow process, comprising:
   a) passing a sample fluid and a carrier fluid into a fluid channel under diffusional split-flow thin cell conditions such that a first component of the sample fluid preferentially flows into a carrier fluid outlet, wherein the sample fluid includes the first component which has a lower molecular weight than a second component in the sample fluid, and wherein the fluid channel comprises an inlet zone, an outlet zone, and a transport region between the inlet zone and outlet zone, said inlet zone including a sample inlet through which the sample fluid passes and a carrier fluid inlet through which the carrier fluid passes, the sample inlet and carrier fluid inlet being fluidly separated by an inlet splitter to minimize mixing of the sample fluid with the carrier fluid in the inlet zone, said transport region being a substantially open rectangular ribbon channel having a sample wall opposite a carrier wall and two side walls bridging the sample wall and carrier wall, said two side walls having a height substantially less than a width of each of the sample wall and carrier wall, so as to form an inlet fluid rich region proximate the sample inlet wall and a carrier fluid rich region proximate the carrier wall and said outlet zone including a sample outlet and the carrier fluid outlet which are fluidly separated by an outlet splitter to segregate portions of the sample fluid and carrier fluid into each of the two outlets as the sample fluid and carrier fluid enter the outlet zone; and
   b) inducing a cross-flow field transversely across the fluid channel under conditions sufficient to augment separation of the first component from the sample fluid while minimizing transfer of the second component into the carrier fluid outlet, said cross-flow field being induced by at least one cross-flow inducer along a wall of the fluid channel in the transport region, said at least one cross-flow inducer directing a cross-flow fluid into the transport region.

11. The method of claim 10, wherein the sample fluid is blood.

12. The method of claim 11, wherein the first component includes at least one of β2 microglobulin, parathyroid hormone, overdose drugs, small proteins, and toxins.

13. The method of claim 11, wherein the second component is human serum albumin.

14. The method of claim 10, wherein the sample fluid is plasma, biological fluid, environmental monitoring sample, or clinical diagnostic sample.

15. The method of claim 10, wherein the carrier fluid is phosphate buffered saline or dialysate fluid.

16. The method of claim 10, wherein the fluid channel is a rectangular ribbon channel.

17. The method of claim 10, wherein the fluid channel is an asymmetrical channel.

18. The method of claim 10, wherein the sample fluid and the carrier fluid have a combined inlet flow rate which is about 1 to about 10 times a flow rate of the cross-flow fluid.

19. The method of claim 10, further comprising applying an electric field across the fluid channel sufficient to reduce diffusion of the second component across the fluid channel.

20. The method of claim 10, wherein the step of injecting the cross flow fluid is a reverse cross-flow from the carrier side to the sample side.

21. The method of claim 10, wherein the sample fluid is blood, and the method further comprises performing hemodialysis on the blood prior to the step of passing the sample fluid and then returning the sample fluid to a patient subsequent to the steps of passing and injecting.

22. A split thin-flow separations device, comprising:
a) a fluid channel having an inlet zone, an outlet zone, and a transport region between the inlet zone and outlet zone, said inlet zone including a sample inlet and a carrier fluid inlet which are fluidly separated by an inlet splitter to minimize mixing of fluids from respective inlets in the inlet zone, said transport region being a substantially open channel having an asymmetrical cross-section, and said outlet zone including a sample outlet and a carrier outlet which are fluidly separated by an outlet splitter to segregate portions of a fluid into each of the two outlets as the fluid enters the outlet zone; and
b) at least one cross-flow inducer along a wall of the fluid channel in the transport region, said at least one cross-flow inducer is oriented to direct a cross-flow fluid into the transport region.

23. A split thin-flow separations device, comprising:
a) a fluid channel having an inlet zone, an outlet zone, and a transport region between the inlet zone and outlet zone, said inlet zone including a sample inlet and a carrier fluid inlet which are fluidly separated by an inlet splitter to minimize mixing of fluids from respective inlets in the inlet zone, said transport region being a substantially open channel, and said outlet zone including a sample outlet and a carrier outlet which are fluidly separated by an outlet splitter to segregate portions of a fluid into each of the two outlets as the fluid enters the outlet zone; and
b) at least one cross-flow inducer along a wall of the fluid channel in the transport region, said at least one cross-flow inducer is oriented to direct a cross-flow fluid into the transport region;
wherein the device is formed as a layered structure including:
a carrier wall plate having the carrier fluid inlet and carrier fluid outlet therein;
a carrier side channel plate oriented adjacent the carrier wall plate having a first open region;
a splitter plate oriented adjacent the carrier side channel plate and forming the inlet splitter and the outlet splitter and a second open region there between;
a sample side channel plate oriented adjacent the splitter plate having a third open region; and
a sample wall plate having the sample inlet and sample outlet therein such that the first open region, the second open region and the third open region collectively form the fluid channel.

* * * * *